United States Patent
Vincent et al.

(10) Patent No.: US 9,429,532 B2
(45) Date of Patent: Aug. 30, 2016

(54) METHOD FOR MONITORING PERFORMANCE OF PROCESS CATALYSTS

(71) Applicant: ExxonMobil Chemical Patents Inc., Baytown, TX (US)

(72) Inventors: Matthew J. Vincent, Kingwood, TX (US); David L. Fletcher, Kingwood, TX (US); Vijay Nanda, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/062,965

(22) Filed: Mar. 7, 2016

(65) Prior Publication Data

US 2016/0187271 A1    Jun. 30, 2016

Related U.S. Application Data

(62) Division of application No. 13/640,344, filed as application No. PCT/US2011/031787 on Apr. 8, 2011, now Pat. No. 9,322,793.

(60) Provisional application No. 61/346,763, filed on May 20, 2010.

(30) Foreign Application Priority Data

Aug. 25, 2010    (EP) .................................... 10173948

(51) Int. Cl.
| | |
|---|---|
| *G01N 25/00* | (2006.01) |
| *C10G 45/08* | (2006.01) |
| *C10G 45/72* | (2006.01) |
| *C07C 2/70* | (2006.01) |
| *B01J 20/08* | (2006.01) |
| *B01J 20/10* | (2006.01) |
| *B01J 20/18* | (2006.01) |
| *B01J 29/70* | (2006.01) |

(52) U.S. Cl.
CPC ............ *G01N 25/00* (2013.01); *C07C 2/70* (2013.01); *C10G 45/08* (2013.01); *C10G 45/72* (2013.01); *B01J 20/08* (2013.01); *B01J 20/10* (2013.01); *B01J 20/18* (2013.01); *B01J 29/70* (2013.01); *C07C 2529/06* (2013.01)

(58) Field of Classification Search
CPC ... G01N 25/00; G01N 25/4846; B01J 20/08; B01J 20/10; B01J 20/18; B01J 29/70; C10G 45/08; C10G 45/72; C01C 2/70; C01C 2529/06
See application file for complete search history.

(56) References Cited

U.S. PATENT DOCUMENTS

| | | | | |
|---|---|---|---|---|
| 5,109,139 A | * | 4/1992 | Dickson | C10G 25/00 208/310 R |
| 5,192,132 A | * | 3/1993 | Pelensky | B01J 8/003 136/230 |
| 6,297,417 B1 | * | 10/2001 | Samson | C07C 2/66 585/448 |
| 6,313,362 B1 | * | 11/2001 | Green | C07C 15/073 585/319 |
| 2008/0139857 A1 | * | 6/2008 | Henn | C07C 2/66 585/310 |
| 2009/0326291 A1 | * | 12/2009 | Jan | C07C 2/66 585/270 |
| 2010/0076237 A1 | * | 3/2010 | Clark | C07C 2/66 585/323 |
| 2011/0076207 A1 | * | 3/2011 | Tirio | C07C 67/08 422/632 |

* cited by examiner

*Primary Examiner* — Lyle Alexander
*Assistant Examiner* — Dwan A Gerido
(74) *Attorney, Agent, or Firm* — Darryl M. Tyus

(57) ABSTRACT

Disclosed is a method for determining when to replace a guard bed material used to remove one or more catalyst poisons from a feed based on a parameter change in a process. A guard bed having a guard bed material is in fluid communication with a catalyst bed having a catalyst. At least three monitors are positioned in said guard bed or said catalyst bed and at least one parameter of the guard bed or catalyst bed is monitored. A feed component comprising one or more catalyst poisons is supplied to said guard bed or said catalyst bed. The feed is contacted with said guard bed material or said catalyst to remove at least a portion of a catalyst poison and to form a product which produces an increase or a decrease in said parameter. The monitored parameters are compared to determine when to replace the guard bed material.

16 Claims, No Drawings

METHOD FOR MONITORING PERFORMANCE OF PROCESS CATALYSTS

CROSS-REFERENCE TO RELATED APPLICATIONS

This application is a divisional of U.S. patent application Ser. No. 13/640,344, filed Dec. 10, 2012, now U.S. Pat. No. 9,322,793, which is a National Stage Application of International Application No. PCT/US2011/031787, filed Apr. 8, 2011, which claims the benefit of and priority to U.S. Provisional Application No. 61/346,763, filed on May 20, 2010, and EP Application No. 10173948.0, filed Aug. 25, 2010, the disclosures of which are incorporated herein by reference in their entireties.

FIELD OF THE INVENTION

The invention relates to a method for monitoring the performance of a guard bed material used to remove a catalyst poison from a feed used in a catalytic process; more particularly, the invention relates to a method for determining when to replace such guard bed material based on a predetermined parameter change in the catalytic process, including, but not limited to, a predetermined change in temperature or pressure.

BACKGROUND OF THE INVENTION

A majority of refining, petrochemical and chemical industrial processes rely upon upstream adsorptive, single or multiple guard beds to adsorb low levels of process contaminants (e.g., catalyst poisons) to protect the catalysts in a downstream reactor.

Japanese Patent Pub. 4198139 discloses a process for producing an alkylbenzene compound by alkylating benzene using a solid acid catalyst, preferably an aluminosilicate, especially zeolite. In order to suppress reduction in activity of the solid acid catalyst caused by basic compounds (e.g., catalyst poisons), benzene is treated to remove basic compounds by contacting the benzene with clay, especially activated clay prepared by acidifying bentonite, or by contacting the benzene with a zeolite, active carbon, silica gel, or alumina.

U.S. Pat. No. 5,109,139 discloses a process for purifying a hydrocarbon feedstock which contains linear paraffins and at least one impurity (e.g., catalyst poisons) selected from the group consisting of aromatic compounds, nitrogen-containing compounds, sulfur-containing compounds, oxygen-containing compounds, color bodies, and mixtures thereof, said process comprising the steps of: a) contacting a liquid feed stream comprising said hydrocarbon feedstock with an adsorbent containing desorbent in an adsorbent bed under conditions comprising temperature and space velocity and for a cycle time suitable for the adsorption of said at least one impurity by said adsorbent to result in an adsorbent cycle effluent comprising purified hydrocarbon feedstock and an amount of said desorbent; b) monitoring said amount of desorbent in said adsorbent cycle effluent to determine a desorbent plateau level which corresponds to a level of said at least one impurity in said feed stream; and c) continuing said monitoring of step b) until said amount of desorbent is detected as dropping below said desorbent plateau level thereby indicating that breakthrough of said at least one impurity is occurring in said adsorbent cycle effluent and that said adsorbent is substantially saturated with said at least one impurity to result in an impurity-loaded adsorbent.

International Pub. WO9807673 discloses a process for preparing an alkylated benzene or mixture of alkylated benzenes which involves contacting a benzene feedstock with a solid acid, such as an acidic clay or acid zeolite, in a pretreatment zone at a temperature greater than about 130° C. but less than about 300° C. to form a pretreated benzene feedstock, and thereafter contacting the pretreated benzene feedstock with (a) alkylating agent in an alkylation zone, or (b) a transalkylating agent in a transalkylation zone, in the presence of an alkylation/transalkylation catalyst so as to prepare the alkylated benzene or mixture of alkylated benzenes. The benzene feedstock may contain impurities (e.g., catalyst poisons), such as oxygen, oxygenates, and nitrogen-containing organic compounds. The pretreatment step improves the lifetime of the alkylation/transalkylation catalyst by removing such impurities from the benzene feedstock.

U.S. Pat. No. 6,313,362 discloses a process in which an alkylation product is contacted with a purification medium in a liquid phase pre-reaction step to remove impurities (e.g., catalyst poisons) and form a purified stream. The purified stream may then be further processed by liquid phase transalkylation to convert the polyaklated aromatic compound to a monoalkylated aromatic compound. The process may use a molecular sieve catalyst such as MCM-22 as the purification medium in the pre-reaction step because of its high reactivity for alkylation, strong retention of catalyst poisons and low reactivity for oligomerization under the pre-reactor conditions. Impurities such as olefins, diolefins, styrene, oxygenated organic compounds, sulfur containing compounds, nitrogen containing compounds, and oligomeric compounds are removed.

U.S. Patent Pub. 2008/0139857 discloses processes suitable for purifying aromatic-containing feed streams, and processes using such purified streams are described, wherein the purification processes comprise: (a) providing a process feed stream comprising an aromatic component and impurities (e.g., catalyst poisons); and (b) bringing the process feed stream into contact with a first zeolite and a second zeolite, wherein the first zeolite has a mean pore size of 0.3 to 0.5 nm, and the second zeolite has a mean pore size of 0.6 to 0.8 nm.

Further, it is disclosed that the catalysts used in alkylation reactions in particular bind impurities very strongly and quickly become exhausted as a result of poisoning when the starting materials are not purified adequately. In the alkylation reaction, which is usually operated continuously, the catalyst is, for example, arranged as a fixed bed. In the case of a fresh catalyst, the reactive zone, i.e., the region within which the exothermic reaction (e.g., of benzene with ethylene to form ethylbenzene) occurs, is at the beginning of the fixed bed, viewed in the flow direction. As the period of operation increases, the reactive "hot" zone travels further along in the flow direction, since the beginning of the catalyst bed becomes increasingly laden with the impurities and thus deactivated, i.e., is no longer catalytically effective. When the reactive zone finally arrives at the end (outlet) of the fixed bed, the total amount of catalyst has become deactivated.

It is disclosed that this effect can, for example, be measured by means of temperature measurements in the fixed catalyst bed: temperature measurement points located in succession along the fixed bed in the flow direction show the profile of the exothermic reaction over the fixed bed. If the temperature at the beginning of the fixed bed rises sharply, based on the temperature of the feed stream, a significant part of the conversion occurs here. If the temperature increase at the beginning of the fixed bed is small but that further downstream is high, the reaction has moved downstream. (If the temperature does not also increase at the end of the fixed bed, the catalyst bed is exhausted over its entire length and has to be replaced or regenerated.)

European Patent Pub. 2110368 discloses a process for the alkylation of an aromatic substrate (e.g., alkylation of benzene with ethylene), and a process for the transalkylation of polyalkylated aromatic components (e.g., transalkylation of diethylbenzene with benzene), wherein the nitrogen-containing impurities in the aromatic substrate feedstock and/or the alkylating agent feedstock are monitored in a range 15 wppb to 35 wppm by dry colorimetry.

U.S. Patent Pub. 2009/0326291 discloses a method for treating a hydrogenation feed stream comprising one or more aromatic compounds (e.g., benzene), one or more nitrogen compounds (e.g., catalyst poisons), and one or more unsaturated aliphatic hydrocarbons (e.g., $C_4$-$C_6$ diolefins), the method comprising contacting the hydrogenation feed stream with a hydrogenation catalyst to selectively hydrogenate the unsaturated aliphatic hydrocarbons. In some embodiments, the hydrogenated effluent is contacted with a zeolitic guard bed to remove at least a portion of the one or more nitrogen compounds.

While these references provide methods for monitoring process catalysts or removing catalyst poisons from aromatic feed streams used in catalytic processes, these references, do not provide a method to predict the time in which a guard bed material used to remove a catalyst poison from feed streams should be removed for replacement and/or regeneration. Such guard bed materials, located upstream of and in fluid communication with downstream process catalysts, protect such process catalysts and slowly deactivate due to the accumulation of catalyst poisons. When the catalyst poison capacity of the guard bed material is reached or exceeded, the catalyst poisons then break through the guard bed and contaminate the downstream process catalyst, causing sudden deactivation of such catalysts. This sudden catalyst deactivation can result in significant loss of production, necessitating an unscheduled shut down of the entire process unit for change-out of the process catalysts.

Therefore, there is a need for a method to monitor the real time performance of the guard bed material. Also, there is a need to predict the time in which such guard bed material should be removed for replacement and/or regeneration prior to catalyst poison break through, thereby enabling reliable and seamless production using the process catalyst. This disclosure meets this and other needs.

SUMMARY OF THE INVENTION

One aspect of the present disclosure is a method for determining when to replace a guard bed material used to remove a catalyst poison from a feed based on a parameter change in a process, said method comprising the steps of: (a) providing a guard bed comprising a guard bed material, said guard bed having an inlet and a downstream outlet; (b) placing at least three guard bed monitors proximate said guard bed; wherein a first guard bed monitor is located proximate said inlet to said guard bed; wherein a third guard bed monitor is located downstream of said outlet of said guard bed and, in some embodiments, said third guard bed monitor is located between an outlet of said guard bed and an inlet of said catalyst bed; and wherein one or more second guard bed monitors is located downstream of said inlet of said guard bed and, in some embodiments, said one or more second guard bed monitors is located downstream of said inlet of said guard bed and upstream of said outlet of said guard bed, for example, located between said inlet and said outlet of said guard bed; (c) monitoring at least one guard bed parameter of said guard bed with each of said at least three guard bed monitors; (d) at least intermittently supplying a feed to said guard bed, wherein said feed comprises a catalyst poison; (e) contacting said feed with said guard bed material under suitable guard bed treatment conditions to remove at least a portion of said catalyst poison from said teed and to form a treated feed, wherein said contacting produces an increase or a decrease in said guard bed parameter; (f) determining a first guard bed delta as the absolute value of the difference between said guard bed parameter at said first monitor and said guard bed parameter at said third monitor; (g) determining a second guard bed delta as the absolute value of the difference between said guard bed parameter at said first monitor and said guard bed parameter at said to second monitor; and (h) replacing said guard bed material when the ratio of said second guard bed delta to said first guard bed delta is less than 1.

In one or more embodiments, the method further comprises the step of providing a catalyst bed comprising a catalyst, wherein said catalyst bed is located downstream of and in fluid communication with said guard bed. In one or more embodiments, the method further comprises the step of contacting said treated feed with said catalyst under suitable conversion conditions to form a product.

Another aspect of the present disclosure is a method for determining when to replace a guard bed material used to remove a catalyst poison from a feed based on a parameter change in a process, said method comprising the steps of: (a) providing a guard bed comprising a guard bed material; (b) providing a catalyst bed comprising a catalyst, said catalyst bed having an inlet, a downstream outlet and is located downstream of and in fluid communication with said guard bed; (c) placing at least three catalyst bed monitors proximate said catalyst bed; wherein a first catalyst bed monitor is located upstream of said inlet to said catalyst bed and, in some embodiments, said first catalyst bed monitor is located downstream of said outlet of said guard bed and upstream of said inlet of said catalyst bed, for example, located between said outlet of said guard bed and said inlet of said catalyst bed; wherein a second catalyst bed monitor is located downstream of said inlet and upstream of said outlet of said catalyst bed, and, in some embodiments; said second catalyst bed monitor is located between said inlet and said outlet of said catalyst bed; and wherein a third catalyst bed monitor is located downstream of said second catalyst bed monitor and, in some embodiments, said third catalyst bed monitor is located between said second catalyst bed monitor and said outlet of said catalyst bed; (d) monitoring at least one catalyst bed parameter of said catalyst bed with each of said catalyst bed monitors; (e) at least intermittently supplying a feed to said guard bed and said catalyst bed, said feed comprises a catalyst poison; (f) contacting said feed with said guard bed material under suitable guard bed treatment conditions to remove at least a portion of said catalyst poison from said teed and to form a treated feed; (g) contacting said treated feed with said catalyst under suitable conversion conditions to form a product, wherein said contacting produces an increase or a decrease in said catalyst bed parameter; (h) determining a first catalyst bed delta as the absolute value of the difference between said catalyst bed parameter at said first catalyst bed monitor and said catalyst bed parameter at said third catalyst bed monitor; (i) determining a second catalyst bed delta as the absolute value of the difference between said catalyst bed parameter at said first monitor and said catalyst bed parameter at said second catalyst bed monitor; and (j) replacing said guard bed material when the ratio of said second catalyst bed delta to said first catalyst bed delta is less than 1.

In one or more embodiments, the guard bed material is a solid acid. Preferably, the solid acid is selected from the group consisting of: acidic aluminas, acidic silicas, silica-aluminas, clays, zeolites, and mesoporous aluminosilicates.

In one or more embodiments, the guard bed parameter or the catalyst bed parameter is temperature and the guard bed monitor or the catalyst bed monitor is a temperature measuring device. In one or more embodiments, the guard bed parameter or the catalyst bed parameter is pressure and the guard bed monitor or the catalyst bed monitor is a pressure measuring device.

In one or more embodiments, the process is an aromatic alkylation process, the catalyst is an alkylation catalyst, the feed further comprises an alkylatable aromatic component and an alkylating agent component, and the treated feed and/or the product comprises an alkylated aromatic component.

In one or more embodiments, the alkylation catalyst comprises a molecular sieve having unit cells of MWW framework topology and characterized by an X-ray diffraction pattern including d-spacing maxima at 12.4±0.25, 3.57±0.07, and 3.42±0.07 Angstroms. Preferably, the alkylation catalyst comprises a molecular sieve selected from the group consisting of MCM-22 family molecular sieve, zeolite beta, faujasite, zeolite Y, Ultrastable Y (USN), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20, and combinations thereof.

In one or more embodiments, the catalyst bed parameter is pressure and said catalyst bed monitor is a pressure measuring device, the catalyst is a hydrotreatment catalyst, said process is a hydrotreatment process, said feed further comprises a sulfur-containing hydrocarbon and hydrogen, and said treated teed comprises a de-sulfurized hydrocarbon. The hydrotreatment catalyst comprises cobalt and molybdenum.

DETAILED DESCRIPTION OF THE INVENTION

Definitions

The term "alkylatable aromatic compound" as used herein means an aromatic compound that may receive an alkyl group. One non-limiting example of an alkylatable aromatic compound is benzene.

The term "alkylated aromatic compound(s)" as used herein means mono-alkylated aromatic compound(s) and poly-alkylated aromatic compound(s).

The term "alkylating agent" as used herein means a compound which may donate an alkyl group to an alkylatable aromatic compound. Non-limiting examples of an alkylating agent are ethylene, propylene, and butylene. Another non-limiting example is any poly-alkylated aromatic compound, defined herein, that is capable of donating an alkyl group to an alkylatable aromatic compound.

The term "aromatic" as used herein in reference to the alkylatable aromatic compounds which are useful herein is to be understood in accordance with its art-recognized scope which includes substituted and unsubstituted mono- and polynuclear compounds. Compounds of an aromatic character which possess a heteroatom (e.g., N or S) are also useful provided they do not act as a catalyst poison, as defined below, under the reaction conditions selected.

The term "catalyst poison" as used herein means one or more impurity or impurities, defined herein, which acts to reduce the cycle-length of a molecular sieve or zeolite catalyst.

The term "conversion conditions" as used herein means conditions, which include, but are not limited to, hydrotreatment conditions, guard bed treatment conditions, alkylation conditions or transalkylation conditions.

The term "hydrotreatment conditions" as used herein include the temperature, or pressure, or amount of sulfur-containing hydrocarbon, or amount of hydrogen, or the WHSV (i.e., weight hourly space velocity) which are suitable to convert at least 1 wt. % of the sulfur-containing hydrocarbon to the de-sulfurized hydrocarbon (based on the total sulfur-containing hydrocarbon in the relevant feed). Preferably, at least 10 wt. % of sulfur-containing hydrocarbons are converted to the de-sulfurized hydrocarbon (based on the total sulfur-containing hydrocarbons in the relevant feed).

The term "guard bed treatment conditions" as used herein include the temperature, or pressure, or amount of alkylatable aromatic compound(s), or amount of alkylating agent(s) (if any), or WHSV, which are suitable to remove at least 1 wt. % of the catalyst poison from the feed (based on the total amount of catalyst poison in the relevant feed). Preferably, at least 10 wt. % of the catalyst poison is removed from the feed (based on the total amount of catalyst poison in the relevant feed).

The term "alkylation conditions" as used herein include the temperature, or pressure, or amount of alkylatable aromatic compound(s), or amount of alkylating agent(s), or WHSV, which are suitable to convert at least 1 wt. % of the alkylatable aromatic compound(s) to mono-alkylated aromatic compounds(s) (based on the total amount of alkylatable aromatic compound(s) in the relevant feed). Preferably, at least 10 wt. % of the alkylatable aromatic compound is converted to mono-alkylated aromatic compounds(s) (based on the total amount of catalyst poison in the relevant feed).

The term "transalkylation conditions" as used herein include the temperature, or pressure, or amount of alkylatable aromatic compound(s), or amount of poly-alkylating aromatic compound(s), or WHSV, which are suitable to convert at least 1 wt. % of the poly-alkylatable aromatic compound(s) to the mono-alkylated aromatic compound(s) (based on the total alkylatable aromatic compound(s) in the feed). Preferably, at least 10 wt. % of the poly-alkylatable aromatic compound(s) is converted to the mono-alkylated aromatic compound(s) (based on the total amount of catalyst poison in the relevant feed).

The term "cycle length" as used herein means the total on-oil time between regenerations, or the on-oil time period between fresh load and regeneration for the guard bed material and/or catalyst. After the fresh or regenerated guard bed material and/or catalyst being brought on-oil, the catalyst may be deactivated due to deposition of coke or catalyst poison.

The term "downstream" as used herein with respect to the location of an item relative to the direction of flow of a stream means that the item is located in the same direction of flow of the stream.

The term "framework type" as used herein has the meaning described in the "Atlas of Zeolite Framework Types," by Ch. Baerlocher, W. M. Meier, and D. H. Olson (Elsevier, 5th Ed., 2001).

The numbering scheme for the elements of the Periodic Table Groups as used herein has the meaning described in the Periodic Table of Elements as published by International Union of Pure and Applied Chemistry on 22 Jun. 2007.

The terms "impurity" or "impurities" as used herein include, but are not limited to, compounds having at least one of the following elements: nitrogen, halogens, oxygen, sulfur, arsenic, selenium, tellurium, phosphorus, and Group 1 through Group 12 metals.

The term "inlet" as used herein means the conduit through which a fluid enters a reactor, including, but not limited to, a guard bed or a catalyst bed.

The term "M41S family molecular sieve" as used herein means a M41S family mesoporous molecular sieve described in J. Amer. Chem. Soc., 1992, 114, 10834.

The term "MCM-22 family material" (or "MCM-22 family molecular sieve"), as used herein, includes:

(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier, and D. H. Olson (Elsevier, 5th Ed., 2001);

(ii) molecular sieves made from a common second degree building block, a 2-dimensional tiling of such MWW framework type unit cells, forming a "monolayer of one unit cell thickness," preferably the one unit cell thickness in the c-direction;

(iii) molecular sieves made from common second degree building blocks, "layers of one or more than one unit cell thickness," wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07, and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07, and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

The term "mono-alkylated aromatic compound(s)" means an aromatic compound that has only one alkyl substituent. Non-limiting examples of mono-alkylated aromatic compounds are ethylbenzene, isopropylbenzene (i.e., cumene) and sec-butylbenzene.

The term "on-oil" as used herein is to be understood as the time the guard bed material and/or catalyst is under conversion conditions.

The term "outlet" as used herein means the conduit through which a fluid exits a reactor, including, but not limited to, a guard bed or a catalyst bed.

The term "poly-alkylated aromatic compound(s)" as used herein means an aromatic compound that has more than one alkyl substituent A non-limiting example of a poly-aklated aromatic compound is poly-aklated benzene, e.g., di-ethylbenzene, tri-ethylbenzene, di-isopropylbenzene, and tri-isopropyibenzene.

The term "proximate" as used herein with respect to the location of a monitor relative to another structure means that the monitor is located either immediately preceding or immediately following such structure.

The term "regenerate" as used herein means techniques whereby a spent or used catalyst is contacted at elevated temperature with an oxygen-containing gas and/or steam to remove carbonaceous deposits and poisons thereon.

The term "upstream" as used herein with respect to the location of an item relative to the direction of flow of a stream means that the item is located in the opposite direction of flow of the stream.

As used herein, the term "intermittently" when used in connection with optionally supplying an alkylating agent stream to said treatment zone means that the alkylating agent is supplied to the treatment zone at intervals from at least 1 hour up to 24 hours or more and then interrupted for periods of 10 to 15 days or more. Importantly, the number of cycles of use is not limited and may be applied as often as needed to monitor the ageing rate.

Feedstocks and Products

Suitable unsubstituted aromatic compounds that may be used for this disclosure include benzene, naphthalene, anthracene, naphthacene, perylene, coronene, and phenanthrene, with benzene being preferred.

Substituted aromatic compounds which may be used for the disclosure should possess at least one hydrogen atom directly bonded to the aromatic nucleus. The aromatic rings may be substituted with one or more alkyl, aryl, alkaryl, alkoxy, cycloalkyl, halide, and/or other groups which do not interfere with the alkylation reaction. Generally the alkyl groups which can be present as substituents on the aromatic compound contain from 1 to about 22 carbon atoms and usually from about 1 to 8 carbon atoms, and most usually from about 1 to 4 carbon atoms.

Suitable substituted aromatic compounds that may be used for this disclosure include, but are not limited to: toluene, xylene, isopropylbenzene, normal propylbertzene, alpha-methylnaphthalene, ethylbenzene, mesitylene, durene, cymenes, butylbenzene, pseudocumene, o-diethylbenzene, m-diethylbenzene, p-diethylbenzene, isoamyl-benzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene.

Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include, but are not limited to, hexylbenzene, nonylbenzene, dodecylbenzene, pentadecylbenzene, hexyltoluene, nonyholuene, dodecyholuene, pentadecytoluene, and the like. Very often alkylate is obtained as a high boiling fraction in which the alkyl group attached to the aromatic nucleus varies in size from about $C_6$ to about $C_{16}$.

Reformate streams that may contain substantial quantities of benzene, toluene and/or xylene may be particularly suitable as an alkylatable aromatic feed for the process of this disclosure. Although the process is particularly directed to the production of ethylbenzene, it is equally applicable to the production of other $C_7$-$C_{20}$ alkylaromatic compounds, such as cumene, as well as $C_{6+}$ alkylaromatics, such as $C_8$-$C_{16}$ linear and near linear alkylbenzenes (e.g., an alkylaromatic).

Suitable hydrogenation feed streams that may be used in this disclosure comprise one or more aromatic compounds and one or more unsaturated aliphatic compounds (e.g., diolefins), in addition to one or more nitrogen compounds. A representative hydrogenation feed component has a Bromine Number of at least about 0.03, typically in the range from about 0.03 to about 1.0, and often in the range from about 0.10 to about 0.75. The Bromine Number (i.e., the extent to which a sample can be brominated, in grams of bromine conswned/100 grams of sample) is a measure of the degree of unsaturation of a hydrocarbon component, and may be determined according to ASTM D1159. Alternatively, the Bromine Number may be the calculated from the theoretical bromine consumption (in grams of bromine per 100 grams of sample) of $C_4$-$C_6$ olefins and diolefins, acetylene, and other unsaturated (non-aromatic) compounds (e.g., cyclopentadiene) in the hydrogenation feed component, based on a GC analysis used to determine the weight percentages of these compounds.

Suitable alkylating agent(s) that may be used in this disclosure comprise alkene compound(s), alcohol compound(s), and/or alkylbenzene(s), and mixtures thereof. Other suitable alkylating agents that may be useful in the process of this disclosure generally include, but are not limited to, any aliphatic or aromatic organic compound having one or more available alkylating aliphatic groups capable of reaction with the alkylatable aromatic compound. Examples of suitable alkylating agents are $C_2$-$C_{16}$ olefins, such as $C_2$-$C_5$ olefins, including ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; ($C_2$-$C_{20}$ ethers, e.g., $C_2$-$C_5$ ethers including dimethyl ether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides; polyalkylated aromatic compound(s), e.g., di-alkylated benzenes (e.g., di-ethylbenzene(s) or di-isopropylbenzenes) and tri-alkylated benzene(s) (e.g., tri-ethylbenzenes or tri-isopropylbenzenes), and so forth. Thus the alkylating agent may preferably be selected from the group consisting of $C_2$-$C_5$ olefins, $C_1$-$C_5$ alkanols, di-ethylbenzene(s), di-isopropylbenzene(s), tri-ethylbenzene(s) and/or tri-isopropylbenzene(s).

Guard Bed Material and Catalysts

In one or more embodiments, the guard bed material is a solid acid. Preferably, the solid acid is selected from the group consisting of acidic aluminas, acidic silicas, acidic silica-aluminas, acidic clays, acidic zeolites, and acidic mesoporous aluminosilicates. In other embodiments, the solid acid comprises a molecular sieve selected from the group consisting of ZSM-5, ZSM-11, ZSM-35, clinoptilolite, ferrierite, stilbite EU-1, NU-87, mordenite, omega, beta, faujasites, gmelinite, ZSM-12, cancrinite, zeolite L, ERB-1, ITQ-1, ITQ-2, ITQ-30, PSH-3, SSZ-25, MCM-22, MCM-36, MCM-49, MCM-56, UZM-8, EMM-10, EMM-12 and EMM-13.

In one or more embodiments, the guard bed material and/or the catalyst comprises a molecular sieve selected from the group consisting of a M41S family molecular sieve, a MCM-22 family molecular sieve, ETS-10, ETAS-10, ETGS-10, and a molecular sieve having a zeolite framework type comprising at least one of ABW, AET, AFG, AFI, AFX, ANA, AST, ASV, BCT, *BEA, BEC, BIK, BOG, BPH, BRE, CAN, CAS, CDO, CFI, CGS, CHA, -CHI, CON, DAC, DDR, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, IMF, ISV, ITE, ITH, ITW, IWR, IWV, IWW, JBW, KFI, LAU, LEV, LIO, -LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSO, OWE, -PAR, PAU, PHI, PON, RHO, -RON, RRO, RSN, RTE, RTH, RUT, RWR, RWY, SFE, SFF, SFG, SFH, SFN, SFO, SGT, SIV, SOD, SOS, SSY, STF, STI, STT, SZR, TER, THO, TOL, TON, TSC, TUN, UEI, UFI, UOZ, USI, UTL, VET, VNI, VSV, -WEN, and YUG. The asterisk in the code BEA* indicates that zeolite beta is disordered. The most representative polymorph of zeolite beta has been selected as the Framework Type. The hyphen preceding the three letter codes above denotes an interrupted framework.

M41S family mesoporous molecular sieves are described in J. Amer. Chem. Soc., 1992, 114, 10834. Members of the M41S family mesoporous molecular sieve include, but are not limited to, MCM-41, MCM-48 and MCM-50. A member of this class is MCM-41 whose preparation is described in U.S. Pat. No. 5,098,684. MCM-41 is characterized by having a hexagonal structure with a uni-dimensional arrangement of pores having a cell diameter greater than 13 Angstroms. The physical structure of MCM-41 is like a bundle of straws wherein the opening of the straws (the cell diameters of the pores) ranges from 13 to 200 Angstroms. MCM-48 has a cubic symmetry and is described for example in U.S. Pat. No. 5,198,203. MCM-50 has a layered or lamellar structure and is described in U.S. Pat. No. 5,246,689.

MCM-22 family molecular sieves comprise a molecular sieve having unit cells of MWW framework topology and characterized by an X-ray diffraction pattern including d-spacing maxima at 12.4±0.25, 3.57±0.07, and 3.42±0.07 Angstroms. The molecular sieve having unit cells of MWW framework topology may also be characterized by having an X-ray diffraction pattern including d-spacing maxima at 12.4±0.25, 6.9±0.15, 3.57±0.07, and 3.42±0.07 Angstroms (either calcined or as-synthesized).

The zeolitic materials designated by the International Zeolite Association Structure Committee (IZA-SC) as being of the MWW topology are multi-layered materials which have two pore systems arising from the presence of both 10 and 12 membered rings. The Atlas of Zeolite Framework Types currently classes at least five differently named materials as having this same topology include, but are not limited to MCM-22, ERB-1, ITQ-1, PSH-3, and SSZ-25.

The MCM-22 family molecular sieves have been found to be useful in catalysts used in a variety of hydrocarbon conversion processes, including especially, but not limited to, alkylation catalysts used in alkylation processes. Preferably, the catalyst is an alkylation catalyst which comprises a molecular sieve selected from the group consisting of MCM-22 family molecular sieve, zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20, and combinations thereof.

More preferably, the alkylation catalyst comprises a MCM-22 family molecular sieve selected from the group consisting of ERB-1, ITQ-1, ITQ-2, ITQ-30, PSH-3, SSZ- 25, MCM-22, MCM-36, MCM-49, MCM-56, UZM-8, EMM-10, EMM-10P, EMM-12, EMM-13 and mixtures thereof.

MCM-22 is described in U.S. Pat. No. 4,954,325; PSH-3 is described in U.S. Pat. No. 4,439,409; SSZ-25 is described in U.S. Pat. No. 4,826,667; ERB-1 is described in European Patent 0293032; ITQ-1 is described in U.S. Pat. No. 6,077, 498; ITQ-2 is described in International Patent Publication No. WO97/17290; ITQ-30 is described in International Patent Publication No, WO2005118476; MCM-36 is described in U.S. Pat. No. 5,250,277; MCM-49 is described in U.S. Pat. No. 5,236,575; MCM-56 is described in U.S. Pat. No. 5,362,697; and UZM-8 is described in U.S. Pat. No. 6,756,030.

The above molecular sieves may further comprise a binder to form a catalyst composition. The binders which are used in preparing the catalyst compositions include clays, silica, alumina, and mixtures thereof. Specific examples of clays include attapulgite, bentonite, sepiolite, hallovsite, and kaolinite. These molecular sieves and binders can be combined in various ratios but usually the binder is present from 10 to 90 wt % of the catalyst composition.

In some embodiments, the catalyst is a hydrotreatment catalyst for use in a hydrotreatment process. Such hydrotreatment catalyst may include a hydrogenation component and a catalyst support. The hydrogenation component of the hydrogenation catalyst may be derived from a Group 8, Group 9, or Group 10 transition metal, such as platinum, iridium, osmium, palladium, rhodium, ruthenium, nickel, cobalt, iron, and mixtures of two or more thereof. Preferred metals are palladium and platinum. A Group 8, Group 9 or Group 10 transition metal may optionally be mixed with Group 14 metals, preferably tin, and/or a Group 7 metal, preferably rhenium and manganese. Other metals known in the art capable of acting as a hydrogenation component include, but are not limited to, a Group 6 metal, such as tungsten, and molybdenum; a Group 11 metal, such as copper, silver, and gold, either alone, or in combination. Preferably, the hydrotreatment catalyst comprises cobalt and molybdenum. The amount of the hydrogenation component may be in the range of 0.001 to 30 wt. % of the total catalyst, preferably from 0.01 to 5 wt. %.

The hydrogenation component can be exchanged onto the support material, impregnated into it or physically admixed with it. Suitable catalyst support materials are those well known in the art, for example, alumina, silica, clay, carbon, zirconia, titania, and mesoporous molecular sieves, as exemplified by MCM-41 type materials, and mixtures thereof.

The catalyst can be formed into various shapes by means well known in the art. Generally the molecular sieve and binder are combined along with water and optionally one or more additives selected from extrusion aids, dispersion aids, porosity modifiers, and peptizing agents, etc. Examples of these additives are carboxymethylcellulose (e.g., extrusion aid), sodium salt of polyacrylic acid (e.g., dispersion aid), polyethylene (e.g., porosity modifier), nitric acid (e.g., peptizing agent). The molecular sieve, water and optional additive are homogeneously mixed by mulling, kneading, etc. Once a homogeneous mixture is obtained it is formed into shapes such as extrudates, pellets, pills, beads, etc., by means well known in the art. These shaped catalyst compositions will possess the physical and chemical properties necessary for the intended use. For example, crush strength, attrition resistance, surface area, adsorption capacity, etc.

Description of the Method

In one aspect, this disclosure is a method for determining when to replace a guard bed material used to remove a catalyst poison from a feed based on a parameter change in a process. This method comprising the steps of: (a) providing a guard bed comprising a guard bed material, said guard bed having an inlet and a downstream outlet; (b) placing at least three guard bed monitors proximate said guard bed; wherein a first guard bed monitor is located proximate said inlet to said guard bed; wherein a third guard bed monitor is located downstream of said outlet of said guard bed and, in some embodiments, said third guard bed monitor is located between an outlet of said guard bed and an inlet of said catalyst bed; and wherein one or more second guard bed monitors is located downstream of said inlet of said guard bed and, in some embodiments; said one or more second guard bed monitors is located downstream of said inlet of said guard bed and upstream of said outlet of said guard bed, for example, located between said inlet and said outlet of said guard bed; (c) monitoring at least one guard bed parameter of said guard bed with each of said at least three guard bed monitors; (d) at least intermittently supplying a feed to said guard bed, wherein said feed comprises a catalyst poison; (e) contacting said feed with said guard bed material under suitable guard bed treatment conditions to remove at least a portion of said catalyst poison from said feed and to form a treated feed, wherein said contacting produces an increase or a decrease in said guard bed parameter; (f) determining a first guard bed delta as the absolute value of the difference between said guard bed parameter at said first monitor and said guard bed parameter at said third monitor; (g) determining a second guard bed delta as the absolute value of the difference between said guard bed parameter at said first monitor and said guard bed parameter at said second monitor; and (h) replacing said guard bed material when the ratio of said second guard bed delta to said first guard bed delta is less than 1.

In one or embodiments, the method further comprises the steps of providing a catalyst bed comprising a catalyst, wherein said catalyst bed is located downstream of and in fluid communication with said guard bed.

In some embodiments, this method further comprises the steps of contacting the treated feed with said catalyst under suitable conversion conditions to form a product.

In some embodiments, the guard bed material is loaded or placed in said guard bed such that the guard bed material extends from said inlet of said guard bed to said outlet of said guard bed, preferably a downstream outlet of said guard bed.

Preferably, at least one of said second guard bed monitors is placed upstream of and proximate to said outlet of said guard bed. More preferably, at least one of said second guard bed monitors is placed at 50%, or 55%, or 60%, or 65%, or 70%, or 75%, or 80%, or 85%, or 90% of the distance measured from said inlet to said outlet of said guard bed. Most preferably, at least one of said second guard bed monitors is placed at 95% of the distance measured from said inlet to said outlet of said guard bed.

The location where the second guard bed monitor is to be placed in the guard bed may be determined as follows. The length of the guard bed is measured from the inlet to the outlet. Then the desired location of the guard bed monitor as a percentage of the distance from the inlet to the outlet is chosen. The length of the guard bed is multiplied by the percentage and then divided by 100 to yield the distance the guard bed monitor is to be placed from the inlet. For example, if the guard bed is 1000 millimeters in length from the inlet to the outlet and the guard bed monitor is to be placed at 95% of the distance from the inlet to the outlet, then the guard bed monitor is place 950 millimeters from the inlet.

In one or more embodiments, said ratio of said second guard bed delta to said first guard bed delta is less than one. That is, the ratio is determined by dividing the second guard bed delta by the first guard bed delta. More preferably, this ratio is selected from the group consisting of 0.9, 0.8, 0.7, 0.6, 0.5, 0.4, 0.3, 0.2 and 0.1, Most preferably, this ratio is selected from the group consisting of 0.9, 0.8, 0.7, 0.6 and 0.5.

When the guard bed parameter is temperature, said guard bed monitor is a temperature measuring device, such as a thermocouple, a thermistor, or a thermometer. When the guard bed parameter is pressure, said guard bed monitor is a pressure measuring device, such as a pressure gauge or a pressure transducer.

In some embodiments, said catalyst is an alkylation catalyst, said process is an aromatic alkylation process, said feed further comprises an alkylatable aromatic component and an aklating agent component, said catalyst poison comprises an impurity having at least one of the following elements: nitrogen, halogens, oxygen, sulfur, arsenic, selenium, tellurium, phosphorus, and Group 1 through Group 12 metals, and said treated feed comprises an alkylated aromatic component. In such case, preferably the guard bed parameter is temperature, and said guard bed monitor is a thermocouple.

Preferably, the alkylatable aromatic component comprises benzene. Preferably, the alkylating agent component comprises ethylene and said alkylated aromatic component comprises ethylbenzene, or said alkylating agent component comprises propylene and said alkylated aromatic component comprises cumene, or said alkylating agent component comprises butene and said alkylated aromatic component comprises sec-butyl benzene.

Preferably, when said catalyst is a hydrotreatment catalyst, said process is a hydrotreatment process, said feed further comprises a sulfur-containing hydrocarbon and hydrogen, said catalyst poison comprises an impurity having at least one of the following elements: nitrogen, halogens, oxygen, sulfur, arsenic, selenium, tellurium, phosphorus, and Group 1 through Group 12 metals, said treated feed comprises a de-sulfurized hydrocarbon, said guard bed parameter is pressure, and said guard bed monitor is a pressure measuring device.

In this aspect of the method of this disclosure, a guard bed is provided to determine when to replace a guard bed material used to remove a catalyst poison from a feed based on a parameter change in a process. Preferably, the outlet of the guard bed is upstream of and in fluid communication with the inlet of a catalyst bed located downstream. The guard bed has a guard bed material therein. The catalyst bed has a catalyst therein. At least three guard bed monitors are placed in said guard bed; however, there may be five, ten, twenty or more guard bed monitors placed in said guard bed. In this embodiment, no monitors are place in the catalyst bed. At least one guard bed parameter, preferably temperature or pressure, is monitored with at least three of the at least three guard bed monitors. In the case of three guard bed monitors, for example, all three guard bed monitors will be used to monitor or measure a parameter. In the case of five monitors, for example, at least three of the five monitors will be used to monitor or measure a parameter.

A feed is intermittently supplied to a guard bed. This feed contains an alkylatable aromatic component, such as benzene, along with a catalyst poison, and an alkylation agent, preferably, small amounts of an alkylating agent, such as ethylene or propylene. In the guard bed, at least one catalyst poison is absorbed by and strongly bound to the guard bed material causing it to be at least partially removed from the feed. With increasing on-oil time on stream, the guard bed material becomes spent or exhausted as a result of absorbing amounts of one or more catalyst poisons. When the guard bed is a fixed bed that receives the feed to an inlet and discharges the feed to an outlet, the guard bed material is spent or exhausted along the direction of flow from the inlet to the outlet. When all of the guard bed material is spent or exhausted, one or more of the catalyst poisons break through and enter the downstream catalyst bed, thereby causing deactivation of the catalyst therein. Advantageously, the method of this disclosure provides a method to determine when to replace the guard bed material by monitoring the guard bed, so as to avoid break through of one or more catalyst poisons from the guard bed to the catalyst bed.

When the guard bed parameter is temperature, it can be monitored or measured with respect to at least three positions along the guard bed in the flow direction. These guard bed temperature measurements provide a profile of the exothermic or endothermic reaction along the guard bed. In the case of an exothermic reaction, the guard bed temperature at the inlet of the guard bed should rise sharply over the guard bed temperature of the feed. If the guard bed temperature increase at the inlet is small or non-existent, and the guard bed temperature increase further downstream is higher, this indicates that the majority of the reaction has moved downstream in the direction of flow. If the guard bed temperature does not increase downstream, it indicates that the guard bed material is spent or exhausted across the entire guard bed and should be replaced.

In one or more embodiments, the downstream process is an alkylation process, the catalyst is an alkylation catalyst, and the catalyst bed comprises an alkylation catalyst.

The feed supplied to the guard bed is contacted with the guard bed material under conversion conditions to form a treated feed which produces an increase or decrease in a guard bed parameter. A first delta is determined as the absolute value of the difference between the guard bed parameter at the first guard bed monitor and the guard bed parameter at the third guard bed monitor, A second delta is determined as the absolute value of the difference between the guard bed parameter at the first monitor and the guard bed parameter at the second guard bed monitor. The guard bed material is replaced when the ratio of the first delta to the second delta is less than 1.

The absolute value of the difference between the parameter at the first monitor and the parameter at the third monitor (i.e.; first delta) represents the largest parameter change in the guard bed. The absolute value of the difference between the parameter at the first monitor and the one or more second monitors (i.e., second delta) represents the first portion of the guard bed that will become deactivated and exhausted as the feed is contacted with the guard bed material. Such deactivation will proceed from the inlet to the outlet of the guard bed with increasing on-oil time on stream, (e.g., a deactivation front). At the start-up of the guard bed, the first delta and the second delta will be approximately the same, so that the ratio of the second delta divided by the first delta will be approximately 1. As the deactivation front proceeds, the second delta will decrease in value, while the first delta will remain fixed; hence, the ratio of the second delta to the first delta will be approximately 1 at start-up and gradually decrease to less than 1 with increasing on-oil time on stream. When the ratio of the second delta to the first delta is less than one, the guard bed material is becoming exhausted as should be replaced. Up until this time, the guard bed material is removing one or more catalyst poisons before they negatively impact the catalyst in the downstream catalyst bed. As such, the guard bed is "protecting" the downstream catalyst bed, leading to longer cycle lengths for the catalyst bed.

In another aspect, this disclosure is a method for determining when to replace a guard bed material used to remove a catalyst poison from a feed based on a parameter change in a process, said method comprising the steps of: (a) providing a guard bed comprising a guard bed material; (b) providing a catalyst bed located downstream of and in fluid communication with said guard bed, wherein said catalyst bed comprising a catalyst and having an inlet, and a downstream outlet; (c) placing at least three catalyst bed monitors proximate said catalyst bed; wherein a first catalyst bed monitor is located upstream of said inlet to said catalyst bed and, in some embodiments, said first catalyst bed monitor is located downstream of said outlet of said guard bed and upstream of said inlet of said catalyst bed, for example, located between said outlet of said guard bed and said inlet of said catalyst bed; wherein a second catalyst bed monitor is located downstream of said inlet and upstream of said outlet of said catalyst bed, and, in some embodiments, said second catalyst bed monitor is located between said inlet and said outlet of said catalyst bed; and wherein a third catalyst bed monitor is located downstream of said second catalyst bed monitor and, in some embodiments, said third catalyst bed monitor is located between said second catalyst bed monitor and said outlet of said catalyst bed; (d) monitoring at least one catalyst bed parameter of said catalyst bed with each of said catalyst bed monitors; (e) at least intermittently supplying a feed to said guard bed and said catalyst bed, wherein said feed comprises a catalyst poison; (f) contacting said feed with said guard bed material under suitable guard bed treatment conditions to remove at least a portion of said catalyst poison from said feed and to form a treated feed; (g) contacting said treated feed with said catalyst under suitable conversion conditions to form a product, wherein said contacting produces an increase or a decrease in said catalyst bed parameter; (h) determining a first catalyst bed delta as the absolute value of the difference between said catalyst bed parameter at said first catalyst bed monitor and said catalyst bed parameter at said third catalyst bed monitor; (i) determining a second catalyst bed delta as the absolute value of the difference between said catalyst bed parameter at said first monitor and said catalyst bed parameter at said second catalyst bed monitor; and (j) replacing said guard bed material when the ratio of said second catalyst bed delta to said first catalyst bed delta is less than 1.

In some embodiments, said catalyst is loaded in said catalyst bed such that said catalyst extends from said inlet of said catalyst bed to said outlet of said catalyst bed, preferably a downstream outlet of said catalyst bed.

Preferably, said second catalyst bed monitor is placed downstream of and proximate to said inlet to said catalyst bed. More preferably, said second catalyst bed monitor is placed at 1%, or 5% or 10%, or at 15%, or 20%, or 25% of the distance measured from said inlet to said outlet of said catalyst bed. Most preferably, said second catalyst bed monitor is place at the inlet (i.e., 0% of the distance measured from said inlet to said outlet of said catalyst bed).

The location where the second catalyst bed monitor is to be placed in the catalyst bed may be determined as follows. The length of the catalyst bed is measured from the inlet to the outlet. Then the desired location of the catalyst bed monitor as a percentage of the distance from the inlet to the outlet is chosen. The length of the catalyst bed is multiplied by the percentage and then divided by 100 to yield the distance the catalyst bed monitor is to be placed from the inlet. For example, if the catalyst bed is 1000 millimeters in length from the inlet to the outlet and the catalyst bed monitor is to be placed at 1% of the distance from the inlet to the outlet, then the catalyst bed monitor is place 10 millimeters from the inlet.

In one or more embodiments, said ratio of said second catalyst bed delta to said first catalyst bed delta is less than 1. That is, the ratio is determined by dividing the second guard bed delta by the first guard bed delta. More preferably, this ratio is selected from the group consisting, of 0.9, 0.8, 0.7, 0.6, 0.5, 0.4, 0.3, 0.2 and 0.1. Most preferably, this ratio is selected from the group consisting of 0.9, 0.8, and 0.7.

When the catalyst bed parameter is temperature, said catalyst bed monitor is a temperature measuring device, such as a thermocouple, a thermistor, or a thermometer. When the catalyst bed parameter is pressure, said catalyst bed monitor is a pressure measuring device, such as a pressure gauge or a pressure transducer.

In some embodiments, said catalyst is an alkylation catalyst, said process is an aromatic alkylation process, said feed further comprises an alkylatable aromatic component and an alkylating agent component, said catalyst poison comprises an impurity having at least one of the following elements: nitrogen, halogens, oxygen, sulfur, arsenic, selenium, tellurium, phosphorus, and Group 1 through Group 12 metals, and said treated feed comprises an alkylated aromatic component. In such case, preferably the catalyst bed parameter is temperature, and said catalyst bed monitor is a thermocouple.

Preferably, the alkylatable aromatic component comprises benzene. Preferably, the alkylating agent component comprises ethylene and said alkylated aromatic component comprises ethylbenzene, or said alkylating agent component comprises propylene and said alkylated aromatic component comprises cumene, or said alkylating agent component comprises butene and said alkylated aromatic component comprises sec-butyl benzene.

Preferably, when said catalyst is a hydrotreatment catalyst, said process is a hydrotreatment process, said feed further comprises a sulfur-containing hydrocarbon and hydrogen, said catalyst poison comprises an impurity having at least one of the following elements: nitrogen, halogens, oxygen, sulfur, arsenic, selenium, tellurium, phosphorus, and Group 1 through Group 12 metals, said treated feed comprises a de-sulfurized hydrocarbon, said catalyst bed parameter is pressure, and said catalyst bed monitor is a pressure measuring device.

In this aspect of the method of this disclosure for determining when to replace a guard bed material in a guard bed based on a parameter change in a process, a catalyst bed is provided downstream of and in fluid communication with a guard bed. Preferably, the inlet of the catalyst bed communicates with the outlet of the guard bed located upstream. The guard bed has a guard bed material therein and the catalyst bed has a catalyst therein. At least three catalyst bed monitors are placed in the catalyst bed; however, there may be five, ten, twenty or more catalyst bed monitors placed in said catalyst bed. In this embodiment, no monitors are place in the guard bed.

At least one catalyst bed parameter, preferably temperature or pressure, of the catalyst bed is monitored with at least three of the at least three monitors. In the case of three monitors, for example, all three monitors will be used to monitor or measure a parameter. In the case of five monitors, for example, at least three of the five monitors will be used to monitor or measure a parameter.

A feed is supplied to a guard bed. This feed contains an alkylatable aromatic component, such as benzene, along with at least one catalyst poison, and small amounts of an alkylating agent, such as ethylene or propylene. In the guard bed, one or more of the catalyst poisons are absorbed by and strongly bound to the guard bed material and at least partially removed from the feed. With increasing on-oil time on stream, the guard bed material becomes spent or exhausted as a result of absorbing one or more of the catalyst poisons. When the guard bed is a fixed bed that receives the teed to an inlet and discharges the teed to an outlet, the guard bed material is spent or exhausted along the direction of flow from the inlet to the outlet. When all of the mud bed material is spent or exhausted, one or more of the catalyst poisons break through and enter the downstream catalyst bed, thereby causing deactivation of the catalyst therein. Advantageously, the method of this disclosure provides a method to determine when to replace the guard bed material by monitoring the catalyst bed (rather than monitoring the guard bed as discussed above), so as to avoid break through of one or more of the catalyst poisons from the guard bed to the catalyst bed. After removal of at least a portion of the one or more catalyst poisons, such feed is supplied to the catalyst bed.

When the catalyst bed parameter is temperature, it can be monitored or measured with respect to at least three positions along the catalyst bed in the flow direction. These catalyst bed temperature measurements provide a profile of the exothermic or endothermic reaction along the catalyst bed. In the case of an exothermic reaction, the catalyst bed temperature at the inlet of the guard bed should rise sharply over the temperature of the feed. If the catalyst bed temperature increase at the inlet is small or non-existent, and the catalyst bed temperature increase further downstream is higher, this indicates that the majority of the reaction has moved downstream in the direction of flow. If the catalyst bed temperature does not increase downstream, it indicates that the guard bed material is spent or exhausted across the entire guard bed and should be replaced.

In one or more embodiments, the downstream process is an alkylation process, the catalyst is an alkylation catalyst, and the catalyst bed comprises an alkylation catalyst.

The feed supplied to the guard bed is contacted with the guard bed material under conversion conditions to form a treated teed which produces an increase or decrease in a guard bed parameter. A first delta is determined as the absolute value of the difference to between the guard bed parameter at the first guard bed monitor and the guard bed parameter at the third guard bed monitor. A second delta is determined as the absolute value of the difference between the guard bed parameter at the first monitor and the guard bed parameter at the second guard bed monitor. The guard bed material is replaced when the ratio of the first delta to the second delta is less than 1.

The absolute value of the difference between the parameter at the first catalyst bed monitor and the parameter at the third catalyst bed monitor (i.e., first delta) represents the largest parameter change in the catalyst bed. The absolute value of the difference between the catalyst bed parameter at the first catalyst bed monitor and the second catalyst bed monitor (i.e., second delta) represents the first portion of the catalyst bed that will become deactivated and exhausted as the feed is contacted with the catalyst in the catalyst bed. Such deactivation will proceed from the inlet to the outlet of the guard bed with increasing on-oil time on stream, (e.g., a deactivation front) and will proceed towards the catalyst bed. At the start-up of the guard bed, the first delta and the second delta of the catalyst bed will be approximately the same, so that the ratio of the second delta divided by the first delta will be approximately 1. As the deactivation front proceeds through the guard bed and enters the catalyst bed, the second delta will decrease in value, while the first delta will remain fixed; hence, the ratio of the second delta to the first delta will be approximately 1 at start-up and decrease to less than 1 with increasing on-oil time on stream. When the ratio of the second delta to the first delta is less than one, the guard bed material has becoming completely exhausted as should be replaced. Up until this time, the guard bed material is removing one or more of the catalyst poisons before they negatively impact the catalyst in the downstream catalyst bed. As such, the guard bed is "protecting" the downstream catalyst bed, leading to longer cycle lengths for the catalyst bed.

In still another aspect, this disclosure is a method for determining when to replace a guard bed material used to remove a catalyst poison from an alkylation feed based on a temperature change in an alkylation process, said method comprising the steps of (a) providing a guard bed comprising a guard bed material, wherein said guard bed having an inlet and a downstream outlet, and wherein said guard bed material is a solid acid selected from the group consisting of acidic aluminas, acidic silica-aluminas, acidic clays, acidic zeolites, and acidic mesoporous aluminosilicates, wherein said alkylated aromatic compound comprises ethylbenzene, isopropylhenzene or sec-butylbenzene; (b) providing an alkylation catalyst bed comprising an alkylation catalyst, wherein said alkylation catalyst bed located downstream of and in fluid communication with said guard bed, and wherein said alkylation catalyst comprises a molecular sieve having unit cells of MWW framework topology and characterized by an X-ray diffraction pattern including d-spacing maxima at 12.4±0.25, 3.57±0.07, and 3.42±0.07 Angstroms; (c) placing at least three guard bed monitors proximate said guard bed; wherein a first guard bed monitor is located proximate said inlet to said guard bed; wherein a third guard bed monitor is located downstream of said outlet of said guard bed, and in some embodiments, said third guard bed monitor is located between said outlet of said guard bed an inlet to a downstream catalyst bed; and wherein one or more second guard bed monitors located downstream of said inlet of said guard bed, and in some embodiments, said one or more second guard bed monitors are located between said inlet said outlet of said guard bed; (d) monitoring the temperature of said guard bed with each of said at least three guard bed monitors; (e) at least intermittently supplying an alkylation feed to said guard bed, wherein said feed comprises benzene, an alkylating agent and a catalyst poison, wherein said alkylating agent is ethylene, propylene or butylene, and wherein said catalyst poison comprises an impurity having at least one of the following elements: nitrogen, halogens, oxygen, sulfur, arsenic, selenium, tellurium, phosphorus, and Group 1 through Group 12 metals; (f) contacting said alkylation feed with said guard bed material under suitable guard bed treatment conditions to remove at least a portion of said catalyst poison from said alkylation feed and to form a treated alkylation feed, wherein said contacting produces an increase in said guard bed temperature; (g) optionally, contacting said treated alkylation feed with said alkylation catalyst under suitable alkylation conditions to form a product; (h) determining a first guard bed delta as the absolute value of the difference between said guard bed temperature at said first guard bed monitor and said guard bed temperature at said third guard bed monitor; (i) determining a second guard bed delta as the absolute value of the difference between said guard bed temperature at said first guard bed monitor and said guard bed temperature at said second guard bed monitor; and (j) replacing said guard bed material when the ratio of said second guard bed delta to said first guard bed delta is less than 1.

In still yet another aspect, this disclosure is a method for determining when to replace a guard bed material used to remove a catalyst poison from an alkylation feed based on a temperature change in an alkylation process, said method comprising the steps of: (a) providing a guard bed comprising a guard bed material, wherein said guard bed material is a solid acid selected from the group consisting of acidic aluminas, acidic silica-aluminas, acidic clays, acidic zeolites, and acidic mesoporous aluminosilicates, wherein said alkylated aromatic compound comprises ethylbenzene, isopropylbenzene or sec-butylbenzene; (b) providing an alkylation catalyst bed located downstream of and in fluid communication with said guard bed, wherein said alkylation catalyst bed comprising an alkylation catalyst and having an inlet, and a downstream outlet, and wherein said alkylation catalyst comprises a molecular sieve having unit cells of MWW framework topology and characterized by an X-ray diffraction pattern including d-spacing maxima at 12.4±0.25, 3.57±0.07, and 3.42±0.07 Angstroms; (c) placing at least three alkylation catalyst bed monitors proximate said alkylation catalyst bed; wherein a first alkylation catalyst bed monitor is located upstream of said inlet to said alkylation catalyst bed, and in some embodiments, said first alkylation catalyst bed monitor is located downstream of said outlet of said guard bed and upstream of said inlet to said alkylation catalyst bed, for example, between said outlet of said guard bed and said inlet of said alkylation catalyst bed; wherein a second alkylation catalyst bed monitor is located downstream of said inlet of said alkylation catalyst bed, and in some embodiments, said second alkylation catalyst bed monitor is located between said inlet and said outlet of said alkylation catalyst bed; and wherein a third alkylation catalyst bed monitor is located downstream of said second alkylation catalyst bed monitor, and in some embodiments, said third alkylation catalyst bed monitor is located between said second alkylation catalyst bed monitor and said outlet of said alkylation catalyst bed; (d) monitoring the temperature of said alkylation catalyst bed with each of said alkylation catalyst bed monitors; (e) at least intermittently supplying an alkylation feed to said guard bed and said alkylation catalyst bed, wherein said alkylation feed comprises benzene, an alkylating agent and catalyst poisons, wherein said alkylating agent is ethylene, propylene or butylene, and wherein said catalyst poison comprises an impurity having at least one of the following elements: nitrogen, halogens, oxygen, sulfur, arsenic, selenium, tellurium, phosphorus, and Group 1 through Group 12 metals; (f) contacting said alkylation feed with said guard bed material under suitable guard bed treatment conditions to remove at least a portion of said catalyst poison from said alkylation feed and to form a treated alkylation feed; (g) contacting said treated alkylation teed with said alkylation catalyst under suitable alkylation conversion conditions to form a product, wherein said contacting produces an increase in said alkylation catalyst bed temperature; (h) determining a first alkylation catalyst bed delta as the absolute value of the difference between said alkylation catalyst bed temperature at said first alkylation catalyst bed monitor and said alkylation catalyst bed temperature at said third alkylation catalyst bed monitor; (i) determining a second alkylation catalyst bed delta as the absolute value of the difference between said alkylation catalyst bed temperature at said first alkylation catalyst bed monitor and said alkylation catalyst bed temperature at said second alkylation catalyst bed monitor; and (j) replacing said guard bed material when the ratio of said second alkylation catalyst bed delta to said first alkylation catalyst bed delta is less than 1.

The disclosure will now be more particularly described with reference to the following prophetic Examples.

EXAMPLES

Example 1

In an aromatic alkylation process, a guard bed used for removal of catalyst poisons from a feed is placed upstream from and in series with an alkylation reactor (i.e., Alkylator) used for performing an alkylation reaction. The guard bed contains a guard bed material, and the Alkylator contains an alkylation catalyst. The guard bed and the Alkylator may also be in the same vessel. Two or more thermocouples are strategically placed in the adiabatically-operated guard bed to measure the guard bed temperature. The guard bed temperature is used to generate a temperature profile for the guard bed material. From this information, the appropriate timing to replace the guard bed material with either a regenerated guard bed material or a new guard bed material is determined.

For ethylhenzene (EB) synthesis, benzene feed, which may include recycled benzene, either of which may contain catalyst poisons, is first passed through the guard bed to adsorb catalyst poisons and protect the alkylation catalyst in the Alkylator located downstream. A small quantity of olefinic compound, i.e., ethylene for EB synthesis, is fed to the guard bed on a continuous or intermittent basis to remove a portion of catalyst poisons present in the benzene feed. Injection of the olefinic compound is advantageous because it reacts exothermically with the benzene feed in the presence of guard bed material to produce an alkylated aromatic compound, thereby producing a temperature profile having a definite temperature rise (e.g., an exotherm) in the guard bed and the fluid therein. Also, the location of the exotherm in the guard bed indicates the area in which the guard bed material is active and adsorbing catalyst poisons. If a particular region of the guard bed indicates less than an expected exotherm, it is a positive indication that this guard bed material is at least partially deactivated due to adsorbed catalyst poisons. As on-oil time on stream increases, the exotherm tends to move across the guard bed in the direction of fluid flow. Any guard bed material that is known in the art may be used as the guard bed material; preferably the guard bed material is a solid acid, such as an acidic zeolite.

The expected temperature profile for the guard bed is shown in Table 1. The first guard bed delta, $\Delta 1$, is the absolute value of the difference in the guard bed temperature of the thermocouple at P1 and the guard bed temperature of the thermocouple at P5. The second guard bed delta, $\Delta 2$, is the absolute value of the difference in the guard bed temperature of the thermocouple at P1 and the guard bed temperature at the thermocouple at P4. As can be seen, the ratio of the second guard bed delta ($\Delta 2$) divided by the first guard bed delta ($\Delta 1$) is less than the value of 1 at about 48 months time on stream which indicates that the catalyst should be replaced.

TABLE 1

| | On-Oil Time on Stream (months)/Temperature (° C.) | | | | | | | | |
|---|---|---|---|---|---|---|---|---|---|
| Position | 8 mo. | 16 mo. | 24 mo. | 32 mo. | 40 mo. | 48 mo. | 56 mo. | 64 mo. | 72 mo. |
| P1 | 200° C. | 200° C. | 200° C. | 200° C. | 200° C. | 200° C. | 200° C. | 200° C. | 200° C. |
| P2 | 220 | 215 | 210 | 205 | 200 | 200 | 200 | 200 | 200 |
| P3 | 240 | 235 | 230 | 225 | 220 | 215 | 210 | 205 | 200 |
| P4 | 240 | 240 | 240 | 240 | 240 | 235 | 230 | 225 | 220 |
| P5 | 240 | 240 | 240 | 240 | 240 | 240 | 240 | 240 | 240 |
| Δ2 | 40 | 40 | 40 | 40 | 40 | 35 | 30 | 25 | 20 |
| Δ1 | 40 | 40 | 40 | 40 | 40 | 40 | 40 | 40 | 40 |
| $\frac{\Delta 2}{\Delta 1}$ | 1 | 1 | 1 | 1 | 1 | 0.875 | 0.75 | 0.625 | 0.5 |

Comparative Example 1

Benzene is fed to the guard bed as in Example 1, but in which no olefin (i.e., ethylene) is co-fed. Although catalyst poisons are removed from the benzene feed by the guard bed material, there is no indication of what portion of the guard bed material in the guard bed has become deactivated. When the guard bed material is completely deactivated, catalyst poisons are no longer being adequately removed by the guard bed. As a result, the catalyst poisons begin to suddenly elute from or pass through the guard bed, thereby causing sudden deactivation of the alkylation catalyst in the Alkylator.

Comparative Example 2

Benzene and ethylene feeds are fed to the Alkylator only (i.e., there is no guard bed). Since there is no guard bed upstream of the Alkylator in this case, the catalyst poisons are not removed from the feeds. As a result, the alkylation catalyst in the Alkylator is not protected from the catalyst poisons and experiences premature deactivation, leading to early regeneration or replacement. Also, without a guard bed there is no capability to monitor the degree of deactivation in an upstream unit before the alkylation catalyst in the Alkylator is impacted.

Example 2

A hydrocarbon feed containing sulfur is fed to a hydrotreatment reactor having a catalyst bed containing a cobalt/molybdenum catalyst. A guard bed having a guard bed material is placed in series with and upstream of the hydrotreatment reactor and is used to monitor the guard bed material. The hydrotreatment reactor has multiple stages of hydrogen injection. The sulfur in the hydrocarbon feed reacts with hydrogen thereby removing it. The hydrotreatment reaction is endothermic and results in a decrease in temperature. Similar to Example 1, the temperature of the adsorptive guard bed is measured via strategically-placed thermocouples. The temperature profile of the guard bed is monitored and the appearance of a lack of a temperature decrease indicates deactivation of the guard bed material.

Example 3

A hydrocarbon feed is hydrotreated in a hydrotreatment reactor as in Example 2, except that the guard bed pressure of the reactor is monitored. A number of pressure measurement indicators (e.g., pressure transducers or gauges) are located along the length of the guard bed and are used to measure the pressure drop across the guard bed. The hydrocarbon feed enters the guard bed, and as hydrocarbons react in the guard bed, a by-product of coke is formed. The guard bed pressure measurement indicators show an increasing pressure drop across the guard bed with increasing on-oil time on stream. The deactivation of the guard bed material is indicated by the pressure at each pressure transducer slowly increasing.

The expected pressure profile is shown in Table 2. The first guard bed delta, Δ1, is the absolute value of the difference in the guard bed pressure of the pressure transducer at P1 and the guard bed pressure of the pressure transducer at P2. The second guard bed delta, Δ2, is the absolute value of the difference in the guard bed pressure of the pressure transducer at P4 and the guard bed pressure at the pressure transducer at P5. As can be seen, the ratio of the second guard bed delta (Δ2) divided by the first guard bed delta (Δ1) is less than the value of 1 at about 16 months time on stream which indicates that the catalyst should be replaced.

TABLE 2

| | On-oil Time on Stream (months)/Pressure (Kilopascals) | | | | |
|---|---|---|---|---|---|
| Position | 8 mo. | 16 mo. | 24 mo. | 32 mo. | 40 mo. |
| P1 | 340 | 342 | 346 | 352 | 360 |
| P2 | 330 | 332 | 336 | 342 | 348 |
| P3 | 320 | 322 | 326 | 330 | 334 |
| P4 | 310 | 312 | 314 | 316 | 318 |
| P5 | 300 | 300 | 300 | 300 | 300 |
| Δ2 | 10 | 10 | 10 | 10 | 12 |
| Δ1 | 10 | 12 | 14 | 16 | 18 |
| $\frac{\Delta 2}{\Delta 1}$ | 1 | 0.83 | 0.71 | 0.63 | 0.67 |

Comparative Example 3

A hydrocarbon feed is hydrotreated in a hydrotreatment reactor as in Example 3, except that there is no guard bed. The hydrocarbon feed enters the hydrotreatment reactor and a pressure measurement indicator is only placed at the outlet of the hydrotreatment reactor where the outlet pressure is measured. As coke is formed on the catalyst, the overall pressure drop across the hydratreatment reactor increases with on-oil time on stream. Unlike Example 3, the rate at which pressure drop is increasing cannot be ascertained because only inlet and outlet conditions of the hydrotreatment reactor are known. Thus, the rate at which the catalyst is deactivated is not known.

In general, a guard bed may be used to remove catalyst poisons from feed streams and/or to serve as a monitor the performance of the guard bed material may be extended to any readily measurable quantity that yields at least one parameter that may be measured around the guard bed. The measured parameter is not particularly limited, and includes, but is not limited to, temperature and pressure measurement. The profile obtained by measurement of the parameter is used to identify the location of the deactivated guard bed material so that the potential life of the guard bed material may be estimated and deactivation of the downstream catalyst may be mitigated. Planning for guard bed material change-out is also facilitated.

All documents described herein are incorporated by reference herein, including any priority documents and/or testing procedures to the extent they are not inconsistent with this text. As is apparent from the foregoing general description and the specific embodiments. While forms of the invention have been illustrated and described; various modifications can be made without departing from the spirit and scope of the invention. Accordingly, it is not intended that the invention be limited thereby.

Additionally or alternately, the invention can be described by the following embodiments:

1. A method for determining when to replace a guard bed material used to remove a catalyst poison from a feed based on a parameter change in a process, said method comprising the steps of:
(a) providing a guard bed comprising a guard bed material, said guard bed having an inlet and a downstream outlet;
(b) placing at least three guard bed monitors proximate said guard bed, wherein a first guard bed monitor is located proximate said inlet to said guard bed; a third guard bed monitor is located downstream of said outlet of said guard bed, and one or more second guard bed monitors is located downstream of said inlet of said guard bed and upstream of said outlet of said guard bed;
(c) monitoring at least one guard bed parameter of said guard bed with each of said at least three guard bed monitors;
(d) at least intermittently supplying a feed to said guard bed, wherein said feed comprises a catalyst poison;
(e) contacting said feed with said guard bed material under suitable guard bed treatment conditions to remove at least a portion of said catalyst poison from said feed and to form a treated feed, wherein said contacting produces an increase or a decrease in said guard bed parameter;
(f) determining a first guard bed delta as the absolute value of the difference between said guard bed parameter at said first guard bed monitor and said guard bed parameter at said third guard bed monitor;
(g) determining a second guard bed delta as the absolute value of the difference between said guard bed parameter at said first guard bed monitor and said guard bed parameter at said second guard bed monitor; and
(h) replacing said guard bed material when the ratio of said second guard bed delta, to said first guard bed delta is less than 1.

2. The method of embodiment 1, further comprising the steps of:
(i) providing a catalyst bed comprising a catalyst, wherein said catalyst bed is located downstream of and in fluid communication with said guard bed; and
(j) contacting said treated feed with said catalyst under suitable conversion conditions to form a product.

3. The method of embodiment 1, wherein said guard bed material extends from said inlet to said outlet of said guard bed.

4. The method of embodiments 1-3, wherein at least one of said second guard bed monitors is placed upstream of and proximate to said outlet of said guard bed.

5. The method of embodiments 1-3, wherein at least one of said second guard bed monitors is placed at 70%, 80% or 90% of the distance measured from said inlet to said outlet of said guard bed.

6. The method of embodiments 1-5, wherein said ratio of said second guard bed delta to said first guard bed delta is selected from the group consisting of 0.9, 0.8, 0.7, 0.6, and 0.5.

7. The method of embodiments 1-6, wherein said guard bed material is a solid acid.

8. The method of embodiment 7, wherein said solid acid is selected from the group consisting of acidic aluminas, acidic silicas, acidic silica-aluminas, acidic clays, acidic zeolites, and acidic mesoporous aluminosilicates.

9. The method of embodiment 7, wherein said solid acid comprises a molecular sieve selected from the group consisting of ZSM-5, ZSM-11, ZSM-35, clinoptilolite, ferrierite, stilbite, EU-1, NU-87, mordenite, omega, beta, faujasites, gmelinite, ZSM-12, cancrinite, zeolite L, ERB-1, ITQ-1, ITQ-2, ITQ-30, PSH-3, SSZ-25, MCM-22, MCM-36, MCM-49, MCM-56, UZM-8, EMM-10, EMM-12, and EMM-13.

10. The method of embodiments 1-9, wherein said guard bed parameter is temperature and said guard bed monitor is a temperature measuring device, or said guard bed parameter is pressure and said guard bed monitor is a pressure measuring device.

11. The method of embodiments 1-9, wherein said process is an aromatic alkylation process, said catalyst is an alkylation catalyst, said feed further comprises an alkylatable aromatic component and an alkylating agent component, said catalyst poison comprises an impurity having at least one of the following elements: nitrogen, halogens, oxygen, sulfur, arsenic, selenium, tellurium, phosphorus, and Group 1 through Group 12 metals, said treated feed comprises an alkylated aromatic component, and said guard bed parameter is temperature and said guard bed monitor is a temperature measuring device.

12. The method of embodiment 11, wherein said alkylatable aromatic component comprises benzene.

13. The method of embodiments 11-12, wherein said alkylating agent component comprises ethylene and said alkylated aromatic component comprises ethylbenzene, or said alkylating agent component comprises propylene and said alkylated aromatic component comprises cumene, or said alkylating agent component comprises butene and said alkylated aromatic component comprises sec-butyl benzene.

14. The method of embodiments 11-13, wherein said alkylation catalyst comprises a molecular sieve having unit cells of MWW framework topology and characterized by an X-ray diffraction pattern including d-spacing maxima at 12.4±0.25, 3.57±0.07, and 3.42±0.07 Angstroms.

15. The method of embodiments 11-14, wherein said alkylation catalyst is selected from the group consisting of ERB-1, ITQ-1, ITQ-2, ITQ-30, PSH-3, SSZ-25, MCM-22, MCM-36, MCM-49, MCM-56, UZM-8, EMM-10, EMM-10P, EMM-12, EMM-13, and mixtures thereof.

16. The method of embodiments 11-13, wherein said alkylation catalyst is selected from the group consisting of MCM-22 family material, zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20, and combinations thereof.

17. The method of embodiment 1, wherein said process is a hydrotreatment process, said catalyst is a hydrotreatment catalyst, said feed further comprises a sulfur-containing hydrocarbon and hydrogen, said catalyst poison comprises an impurity having at least one of the following elements: nitrogen, halogens, oxygen, sulfur, arsenic, selenium, tellurium, phosphorus, and Group 1 through Group 12 metals, said treated feed comprises a desulfurized hydrocarbon, said guard bed parameter is pressure, said guard bed monitor is a pressure measuring device.

18. The method of embodiment 17, wherein said hydrotreatment catalyst comprises cobalt and molybdenum.

19. A method for determining when to replace a guard bed material used to remove a catalyst poison from a feed based on a parameter change in a process, said method comprising the steps of:
(a) providing a guard bed comprising a guard bed material;
(b) providing a catalyst bed located downstream of and in fluid communication with said guard bed, wherein said catalyst bed comprising a catalyst and having an inlet, and a downstream outlet;
(c) placing at least three catalyst bed monitors proximate said catalyst bed, wherein a first catalyst bed monitor is located upstream of said inlet to said catalyst bed, a second catalyst bed monitor is located downstream of said inlet and upstream of said outlet of said catalyst bed, and a third catalyst bed monitor is located downstream of said second catalyst bed monitor;
(d) monitoring at least one catalyst bed parameter of said catalyst bed with each of said catalyst bed monitors;
(e) at least intermittently supplying a feed to said guard bed and said catalyst bed, wherein said feed comprises a catalyst poison;
(f) contacting said feed with said guard bed material under suitable guard bed treatment conditions to remove at least a portion of said catalyst poison from said feed and to form a treated feed;
(g) contacting said treated feed with said catalyst under suitable conversion conditions to form a product, wherein said contacting produces an increase or a decrease in said catalyst bed parameter;
(h) determining a first catalyst bed delta as the absolute value of the difference between said catalyst bed parameter at said first catalyst bed monitor and said catalyst bed parameter at said third catalyst bed monitor;
(i) determining a second catalyst bed delta as the absolute value of the difference between said catalyst bed parameter at said first catalyst bed monitor and said catalyst bed parameter at said second catalyst bed monitor; and
(j) replacing said guard bed material when the ratio of said second catalyst bed delta to said first catalyst bed delta is less than 1.

20. The method of embodiment 19, wherein said catalyst is loaded in said catalyst bed such that said catalyst extends from said inlet to said outlet of said catalyst bed.

21. The method of embodiments 19-20, wherein said second catalyst bed monitor is placed downstream of and proximate to said inlet to said catalyst bed.

22. The method of embodiments 19-20, wherein said second catalyst bed monitor is placed at 1%, 5%, or 10% of the distance measured from said inlet to said outlet of said catalyst bed.

23. The method of embodiments 19-22, wherein said ratio of said second catalyst bed delta to said first catalyst bed delta is selected from the group consisting of 0.9, 0.8, and 0.7.

24. The method of embodiments 19-23, wherein said guard bed material is a solid acid.

25. The method embodiment 24, wherein said solid acid is selected from the group consisting of acidic aluminas, acidic silica-aluminas, acidic clays, acidic zeolites, and acidic mesoporous aluminosilicates.

26. The method of embodiments 24-25, wherein said solid acid comprises a molecular sieve selected from the group consisting of: ZSM-5, ZSM-11, ZSM-35, clinoptilolite, ferrierite, stilbite, EU-1, NU-87, mordenite, omega, beta, faujasites, gmelinite, ZSM-12, cancrinite, zeolite L, ERB-1, ITQ-1, ITQ-2, ITQ-30, PSH-3, SSZ-25, MCM-22, MCM-36, MCM-49, MCM-56, UZM-8, EMM-10, EMM-12, and EMM-13.

27. The method of embodiments 19-26, wherein said catalyst bed parameter is temperature and said catalyst bed monitor is a temperature measuring device, or said catalyst bed parameter is pressure and said catalyst bed monitor is a pressure measuring device.

28. The method of embodiments 19-26, wherein said catalyst is an alkylation catalyst, said process is an aromatic alkylation process, said feed further comprises an alkylatable aromatic component and an alkylating agent component, said catalyst poison comprises an impurity having at least one of the following elements: nitrogen, halogens, oxygen, sulfur, arsenic, selenium, tellurium, phosphorus, and Group 1 through Group 12 metals, said treated feed comprises an alkylated aromatic component, and said catalyst bed parameter is temperature and said catalyst bed monitor is a temperature measuring device.

29. The method of embodiment 28, wherein said alkylatable aromatic component comprises benzene.

30. The method of embodiments 28-29, wherein said alkylating agent component comprises ethylene and said alkylated aromatic component comprises ethylbenzene, or said alkylating agent component comprises propylene and said alkylated aromatic component comprises cumene, or said alkylating agent component comprises butene and said alkylated aromatic component comprises sec-butyl benzene.

31. The method of embodiments 28-30, wherein said alkylation catalyst comprises a molecular sieve having unit cells of MWW framework topology and Characterized by an X-ray diffraction pattern including d-spacing maxima at 12.4±0.25, 3.57±0.07, and 3.42±0.07 Angstroms:

32. The method of embodiments 28-31, wherein said alkylation catalyst is selected from the group consisting of: EBB-1, ITQ-1, ITQ-2, ITQ-30, PSH-3, SSZ-25, MCM-22, MCM-36, MCM-49, MCM-56, UZM-8, EMM-10, EMM-10P, EMM-12, EMM-13, and mixtures thereof.

33. The method of embodiments 28-30, wherein said alkylation catalyst is selected from the group consisting of MCM-22 family material, zeolite beta, faujasite, zeolite Y, Ultrastable Y (USY), Dealuminized Y (Deal Y), Rare Earth Y (REY), Ultrahydrophobic Y (UHP-Y), mordenite TEA-mordenite, ZSM-3, ZSM-4, ZSM-14, ZSM-18, ZSM-20, and combinations thereof.

34. The method of embodiment 19, wherein said catalyst bed parameter is pressure and said catalyst bed monitor is a pressure measuring device, said catalyst is a hydrotreatment catalyst, said process is a hydrotreatment process, said feed further comprises a sulfur-containing hydrocarbon and hydrogen, and said treated feed comprises a de-sulfurized hydrocarbon:

35. The method of embodiment 34, wherein said hydrotreatment catalyst comprises cobalt and molybdenum.

36. A method for determining when to replace a guard bed material used to remove a catalyst poison from an alkylation feed based on a temperature change in an alkylation process, said method comprising the steps of:
(a) providing a guard bed comprising a guard bed material, wherein said guard bed having an inlet and a downstream outlet, and wherein said guard bed material is a solid acid selected from the group consisting of acidic aluminas, acidic silica-aluminas, acidic clays, acidic zeolites, and acidic mesoporous aluminosilicates, wherein said alkylated aromatic compound comprises ethylbenzene, isopropylbenzene or sec-butylbenzene;
(b) providing an alkylation catalyst bed comprising an alkylation catalyst, wherein said alkylation catalyst bed located downstream of and in fluid communication with said guard bed, and wherein said alkylation catalyst comprises a molecular sieve having unit cells of MWW framework topology and characterized by an X-ray diffraction pattern including d-spacing maxima at 12.4±0.25, 3.57±0.07, and 3.42±0.07 Angstroms;
(c) placing at least three guard bed monitors proximate said guard bed, wherein a first guard bed monitor is located proximate said inlet to said guard bed, a third guard bed monitor is located downstream of said outlet of said guard bed, and one or more second guard bed monitors located downstream of said inlet of said guard bed;
(d) monitoring the temperature of said guard bed with each of said at least three guard bed monitors;
(e) at least intermittently supplying an alkylation feed to said guard bed, wherein said feed comprises benzene, an alkylating agent and a catalyst poison, wherein said alkylating agent is ethylene, propylene or butylene, and wherein said catalyst poison comprises an impurity having at least one of the following elements: nitrogen, halogens, oxygen, sulfur, arsenic, selenium, tellurium, phosphorus, and Group 1 through Group 12 metals;
(f) contacting said alkylation feed with said guard bed material under suitable guard bed treatment conditions to remove at least a portion of said catalyst poison from said alkylation feed and to form a treated alkylation feed, wherein said contacting produces an increase in said guard bed temperature;
(g) determining a first guard bed delta as the absolute value of the difference between said guard bed temperature at said first guard bed monitor and said guard bed temperature at said third guard bed monitor;
(h) determining a second guard bed delta as the absolute value of the difference between said guard bed temperature at said first guard bed monitor and said guard bed temperature at said second guard bed monitor; and
(i) replacing said guard bed material when the ratio of said second guard bed delta to said first guard bed delta is less than 1.

37. A method for determining when to replace a guard bed material used to remove a catalyst poison from an alkylation feed based on a temperature change in an alkylation process, said method comprising the steps of:
(a) providing a guard bed comprising a guard bed material, wherein said guard bed material is a solid acid selected from the group consisting of acidic aluminas, acidic silica-aluminas, acidic clays, acidic zeolites, and acidic mesoporous aluminosilicates, wherein said alkylated aromatic compound comprises ethyl benzene, isopropyl benzene or sec-butylbenzene;
(b) providing an alkylation catalyst bed located downstream of and in fluid communication with said guard bed, wherein said alkylation catalyst bed comprising an alkylation catalyst and having an inlet, and a downstream outlet, and wherein said alkylation catalyst comprises a molecular sieve having unit cells of MWW framework topology and characterized by an X-ray diffraction pattern including d-spacing maxima at 12.4±0.25, 3.57±0.07, and 3.42±0.07 Angstroms;
(c) placing at least three alkylation catalyst bed monitors proximate said alkylation catalyst bed, wherein a first alkylation catalyst bed monitor is located upstream of said inlet to said alkylation catalyst bed, a second alkylation catalyst bed monitor is located downstream of said inlet and upstream of said outlet of said alkylation catalyst bed, and a third alkylation catalyst bed monitor is located downstream of said second alkylation catalyst bed monitor;
(d) monitoring the temperature of said alkylation catalyst bed with each of said alkylation catalyst bed monitors;
(e) at least intermittently supplying an alkylation feed to said guard bed and said alkylation catalyst bed, wherein said alkylation feed comprises benzene, an alkylating agent and catalyst poisons, wherein said alkylating agent is ethylene, propylene or butylene, and wherein said catalyst poison comprises an impurity having at least one of the following elements: nitrogen, halogens, oxygen, sulfur, arsenic, selenium, tellurium, phosphorus, and Group 1 through Group 12 metals;
(f) contacting said alkylation feed with said guard bed material under suitable guard bed treatment conditions to remove at least a portion of said catalyst poison from said alkylation feed and to form a treated alkylation feed;
(g) contacting said treated alkylation feed with said alkylation catalyst under suitable alkylation conversion conditions to form a product, wherein said contacting produces an increase in said alkylation catalyst bed temperature;
(h) determining a first alkylation catalyst bed delta as the absolute value of the difference between said alkylation catalyst bed temperature at said first alkylation catalyst bed monitor and said alkylation catalyst bed temperature at said third alkylation catalyst bed monitor;
(i) determining a second alkylation catalyst bed delta as the absolute value of the difference between said alkylation catalyst bed temperature at said first alkylation catalyst bed monitor and said alkylation catalyst bed temperature at said second alkylation catalyst bed monitor; and
(j) replacing said guard bed material when the ratio of said second alkylation catalyst bed delta to said first alkylation catalyst bed delta is less than 1.

The invention claimed is:
1. A method for determining when to replace a guard bed material used to remove a catalyst poison from an alkylation feed based on a temperature change in an alkylation process, said method comprising the steps of:
(a) providing a guard bed comprising a guard bed material;
(b) providing an alkylation catalyst bed located downstream of and in fluid communication with said guard bed, wherein said alkylation catalyst bed has an inlet, and a downstream outlet;
(c) loading an alkylation catalyst in said alkylation catalyst bed such that said alkylation catalyst extends from said inlet to said outlet of said catalyst bed;
(d) placing at least three alkylation catalyst bed monitors proximate said alkylation catalyst bed, wherein a first alkylation catalyst bed monitor is located upstream of said inlet to said alkylation catalyst bed, a second alkylation catalyst bed monitor is located downstream of said inlet and upstream of said outlet of said alkylation catalyst bed, and a third alkylation catalyst bed monitor is located downstream of said second alkylation catalyst bed monitor;

(e) monitoring the temperature of said alkylation catalyst bed with each of said alkylation catalyst bed monitors;

(f) at least intermittently supplying said alkylation feed to said guard bed and said alkylation catalyst bed, wherein said alkylation feed comprises an alkylatable aromatic component, an alkylating agent component and a catalyst poison;

(g) contacting said alkylation feed with said guard bed material under suitable guard bed treatment conditions to remove at least a portion of said catalyst poison from said alkylation feed and to form a treated alkylation feed comprising an alkylated aromatic component;

(h) contacting said treated alkylation feed with said alkylation catalyst under suitable alkylation conversion conditions to form a product, wherein said contacting produces an increase in said alkylation catalyst bed temperature;

(i) determining a first alkylation catalyst bed delta as the absolute value of the difference between said alkylation catalyst bed temperature at said first alkylation catalyst bed monitor and said alkylation catalyst bed temperature at said third alkylation catalyst bed monitor;

(j) determining a second alkylation catalyst bed delta as the absolute value of the difference between said alkylation catalyst bed temperature at said first alkylation catalyst bed monitor and said alkylation catalyst bed temperature at said second alkylation catalyst bed monitor; and (k) replacing said guard bed material when the ratio of said second alkylation catalyst bed delta to said first alkylation catalyst bed delta is less than 1.

2. The method of claim 1, wherein said second catalyst bed monitor is placed at 1%, 5%, or 10% of the distance measured from said inlet to said outlet of said catalyst bed.

3. The method of claim 1, wherein said ratio of said second catalyst bed delta to said first catalyst bed delta is selected from the group consisting of 0.9, 0.8, and 0.7.

4. The method of claim 1, wherein said catalyst poison comprises an impurity having at least one of the following elements: nitrogen, halogens, oxygen, sulfur, arsenic, selenium, tellurium, phosphorus, and Group 1 through Group 12 metals.

5. The method of claim 1, wherein said alkylation catalyst is selected from the group consisting of zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20, and combinations thereof.

6. The method of claim 1, wherein said guard bed material is a solid acid.

7. The method of claim 6, wherein said solid acid is selected from the group consisting of acidic aluminas, acidic silica-aluminas, acidic clays, acidic zeolites, and acidic mesoporous aluminosilicates.

8. The method of claim 6, wherein said solid acid comprises a molecular sieve selected from the group consisting of ZSM-5, ZSM-11, ZSM-35, clinoptilolite, ferrierite, stilbite, EU-1, NU-87, mordenite, omega, beta, faujasites, gmelinite, ZSM-12, cancrinite, and zeolite L.

9. The method of claim 1, wherein said alkylatable aromatic component comprises benzene.

10. The method of claim 9, wherein said alkylating agent component comprises ethylene and said alkylated aromatic component comprises ethylbenzene.

11. The method of claim 9, wherein said alkylating agent component comprises propylene and said alkylated aromatic component comprises cumene.

12. The method of claim 9, wherein said alkylating agent component comprises butene and said alkylated aromatic component comprises sec-butyl benzene.

13. The method of claim 1, wherein said alkylation catalyst comprises a MCM-22 family material.

14. The method of claim 13, wherein said MCM-22 family material comprises a molecular sieve having unit cells of MWW framework topology.

15. The method of claim 14, wherein said molecular sieve having unit cells of MWW framework topology is characterized by an X-ray diffraction pattern, including d-spacing maxima at 12.4±0.25, 3.57±0.07, and 3.42±0.07 Angstroms.

16. The method of claim 14, wherein said MCM-22 family material is selected from the group consisting of ERB-1, ITQ-1, ITQ-2, ITQ-30, PSH-3, SSZ-25, MCM-22, MCM-36, MCM-49, MCM-56, UZM-8, EMM-10, EMM-10P, EMM-12, EMM-13, and mixtures thereof.

* * * * *